US012758236B2

(12) United States Patent
Scheeh et al.

(10) Patent No.: US 12,758,236 B2
(45) Date of Patent: Oct. 13, 2026

(54) SURGICAL GUIDES WITH REMOVABLE INSERTS

(71) Applicant: OsteoMed LLC, Addison, TX (US)

(72) Inventors: Johanna Scheeh, Euless, TX (US); Devid R. Zille, Addison, TX (US)

(73) Assignee: OsteoMed LLC, Addison, TX (US)

( * ) Notice: Subject to any disclaimer, the term of this patent is extended or adjusted under 35 U.S.C. 154(b) by 9 days.

(21) Appl. No.: 19/076,172

(22) Filed: Mar. 11, 2025

(65) Prior Publication Data

US 2025/0325284 A1 Oct. 23, 2025

Related U.S. Application Data

(63) Continuation of application No. 17/095,570, filed on Nov. 11, 2020, now Pat. No. 12,268,403.

(60) Provisional application No. 62/934,473, filed on Nov. 12, 2019.

(51) Int. Cl.

| | |
|---|---|
| ***A61B 17/17*** | (2006.01) |
| ***A61B 34/10*** | (2016.01) |
| ***B33Y 80/00*** | (2015.01) |
| *B33Y 10/00* | (2015.01) |

(52) U.S. Cl.

CPC .......... *A61B 17/1739* (2013.01); *A61B 34/10* (2016.02); *B33Y 80/00* (2014.12); *A61B 2034/102* (2016.02); *A61B 2034/105* (2016.02); *A61B 2034/108* (2016.02); *B33Y 10/00* (2014.12)

(58) Field of Classification Search

CPC ... A61B 17/15; A61B 17/1739; A61B 17/176; A61B 17/8071; A61B 2017/568; A61B 2034/102; A61B 2034/105; A61B 2034/108; A61B 34/10; A61B 2050/005; A61B 2050/0056; A61B 2050/0065; A61B 50/20; A61B 50/30

See application file for complete search history.

(56) References Cited

U.S. PATENT DOCUMENTS

| | | | |
|---|---|---|---|
| 12,268,403 | B2 | 4/2025 | Scheeh et al. |
| 2006/0200158 | A1 | 9/2006 | Farling et al. |
| 2009/0299369 | A1 | 12/2009 | Orbay et al. |
| 2011/0054528 | A1 | 3/2011 | Michaelson |
| 2019/0076154 | A1 | 3/2019 | Herzog et al. |
| 2020/0315633 | A1 | 10/2020 | Herzog et al. |

(Continued)

FOREIGN PATENT DOCUMENTS

| | | |
|---|---|---|
| WO | WO 2019/072865 A1 | 4/2019 |

OTHER PUBLICATIONS

Orthopedic hardware and equipment for the beginner Part 1. Pins and wires—PMC (Year: 2011).

*Primary Examiner* — Samuel S Hanna

(74) *Attorney, Agent, or Firm* — Knobbe, Martens, Olson, & Bear, LLP

(57) ABSTRACT

The present disclosure describes a surgical guide comprising a cutting guide defining a plurality of cutting slots and including at least one removable insert positioned between the plurality of cutting slots. The at least one removable insert defines an aperture which is designed to receive a surgical fastening device. The surgical guide further comprises a template guide which defines a feature. The at least one removable insert is designed to fit in the template guide at least in part using the feature.

10 Claims, 8 Drawing Sheets

(56) References Cited

U.S. PATENT DOCUMENTS

| | | | | |
|---|---|---|---|---|
| 2020/0375686 | A1* | 12/2020 | Zille | A61B 50/20 |
| 2021/0137537 | A1 | 5/2021 | Zille | |

* cited by examiner

SURGICAL GUIDES WITH REMOVABLE INSERTS

CROSS-REFERENCE TO RELATED APPLICATION

The present application claims priority to U.S. Provisional Application No. 62/934,473 filed Nov. 12, 2019 and entitled "SURGICAL GUIDES WITH REMOVABLE INSERTS," the disclosure of which is incorporated by reference herein in its entirety.

TECHNICAL FIELD

The present disclosure generally relates to reconstruction-related procedures, including methods and systems employed in such procedures. In particular, the disclosure describes surgical guides designed to facilitate positioning of one or more resected bones at a reconstruction site.

BACKGROUND

An osteotomy procedure is generally performed to correct bone-related defects and/or abnormalities. The procedure may include a surgical operation where a surgeon (e.g., an orthopedic surgeon) cuts a bone to shorten, lengthen, change its alignment, or replace a portion of the bone with an implant. For example, an illustrative osteotomy procedure may include surgically cutting or dividing the tibia bone (or a portion thereof) and then shifting the divided ends to change the alignment of the tibia bone. Another illustrative osteotomy procedure may include excising a tumor from a bone, which may include removing the tumorous bone. In some cases, portions of the bone surrounding the tumorous bone may also be removed. Excising the tumorous bone often leads to cosmetic defects, which can have negative effects on the appearance of the patient. To appease the cosmetic defect and improve the patient's lifestyle, surgeons often reconstruct the defect. One of the techniques used for reconstruction is a free flap technique, which includes transplantation of a biological tissue (e.g., bone) from a donor site of the patient's body to a reconstruction site, in order to reconstruct an existing defect.

By way of example, reconstruction of a mandible using the free flap technique is described using FIGS. 1(*a*) and 1(*b*), which depict an anterior view of leg 100 and front-view 120 of a skull, respectively. A surgeon may first finalize a donor site, which may be done by determining whether the characteristics (e.g., cross-section) of one or more bones (also referred to as donor bones) present in the donor site are similar to the characteristics of the patient's original mandible bone. For mandibular reconstruction, the donor bone may be chosen from a variety of bones (e.g., collar bone, hip bone, etc.). For the sake of illustration, it is assumed that the surgeon chooses a fibula as the donor bone to reconstruct the mandible.

Leg 100 includes tibia 105, fibula 110, and guide 115 positioned on fibula 110. The surgeon, using cutting slots, may resect fibula 110 to yield or extract resected bone portions. For example, the surgeon, using cutting slots 111 and 112 may resect fibula 110 to carve out resected bone 115*a*. Similarly, the surgeon, using cutting slots 113 and 114 may carve out resected bone 115*b*, and using cutting slots 116 and 117, the surgeon may carve out resected bone 115*c*. The surgeon may then transplant the resected bones 115*a*, 115*b*, and 115*c* to the mandible. Referring now to FIG. 1(*b*), front-view 120 shows the donor site and a reconstructed mandible using the resected bones 115*a*, 115*b*, and 115*c*. To perform the reconstruction using the free flap technique, the surgeon may first approximate the position and/or placement of resected bone 115*a* on left zygomatic bone 121 and then affix bone 115*a* to the approximated position using surgical fastening devices, e.g., surgical screws and plates (not shown in FIG. 1(*b*)). The surgeon may then choose to approximate the position of resected bone 115*c* on right zygomatic bone 122 and affix resected bone 115*c* at the approximated position using surgical fastening devices. Following that, the surgeon may position and affix resected bone 115*b* between resected bones 115*a* and 115*c*.

Placing the resected bones 115*a*, 115*b*, and 115*c* at their desired positions to reconstruct the mandible is one of the challenging aspects of the free hand technique, partly because of the non-linear (or curved) nature of mandibular bone and the issues associated with accurately positioning multiple resected bones at the reconstruction site. Free hand technique may make the reconstruction even riskier because the possibility of prolonging the period of ischemia (e.g., inadequate blood supply to a part of body) and not restoring correct bone-to-bone contact (e.g., contacts between the resected bones) is high and can ultimately lead to a higher rate of complications and poor esthetic and functional results.

SUMMARY

The present application describes various embodiments of improved surgical guides and methods that may be used by surgeons to perform bone reconstruction-related surgical procedures. The improved surgical guides described herein may include a cutting guide and a template guide. The cutting guide, in embodiments, may be designed to 1) be positioned (and/or affixed) at a donor site and 2) resect one or more bones from the donor site. Whereas, the template guide, in embodiments, may be designed to 1) be positioned (and/or affixed) at the reconstruction site and 2) facilitate positioning and affixing the resected bones accurately.

In embodiments, the cutting guide may include specific parts (e.g., removable inserts) that are designed to secure to a resected bone and couple with the template guide to facilitate the defect reconstruction. The cutting guide may also include a plurality of cutting slots designed to resect the donor bone such that each resected bone has a removable insert secured to it. The template guide may include one or more features (e.g., recesses) that may be designed to couple with the removable inserts (e.g., removable inserts which have resected bones secured onto them) to reconstruct the defect. For example, using cutting guide, a surgeon may carve out resected bones with removable inserts attached to them. Then, by using the template guide, the surgeon may couple the removable inserts to the features on the template guide to perform the defect reconstruction. Using cutting and template guides in conjunction with each other reduce the period of ischemia and facilitate correct bone-to-bone contact (e.g., contacts between the resected bones) and, overall, reduces the rate of complications.

Some of the embodiments described in this application provide for patient-specific surgical guides. In one embodiment, one or more surgical guides are custom designed individually for every patient according to the patient's anatomical model (which is created from various medical imaging techniques (e.g., CT scans, MRI scans, and the like)). Some of the embodiments described in this application provide for semi-custom surgical guides, where the surgical guides may be designed based on age, gender, or generic physical makeup of the human anatomical structure. The present application also describes various embodiments of methods for manufacturing these surgical guides. In some embodiments, the manufacturing process of patient-specific surgical guides may include receiving patient imaging data, which may be used to generate a model. This model may then be used to produce a surgical guide, which may then be manufactured using 3D printing techniques, and the like.

The foregoing has outlined rather broadly the features and technical advantages of the embodiments in order that the detailed description of the embodiments that follows may be better understood. Additional features and advantages of the embodiments disclosed in this application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the embodiments in this application as set forth in the appended claims. The novel features which are believed to be characteristic of the embodiments, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding, reference is now made to the following descriptions taken in conjunction with the accompanying drawings, in which:

FIG. 1(*b*) depicts a front-view of the patient's skull;

DETAILED DESCRIPTION

For the sake of illustration and clarity, this disclosure describes surgical guides that may be used during mandible-related reconstruction procedures using fibula as a donor bone. However, it should be appreciated that the disclosure is not intended to be limited to the examples and designs of surgical guides used for mandible-related procedures or particular donor sites, but is to be accorded the widest scope consistent with the principles and novel features of the surgical guides disclosed ahead. Thus, the description ahead is provided to enable any person skilled in the art to make or use the disclosure. Various modifications to the disclosure will be readily apparent to those skilled in the art, and the generic principles of the use and manufacturing of surgical guides defined herein may be applied to other variations as well (e.g., using the invention while performing a different reconstruction procedures (e.g., maxillary-related) using different donor bones (e.g., collar bone)).

Figure 1A:
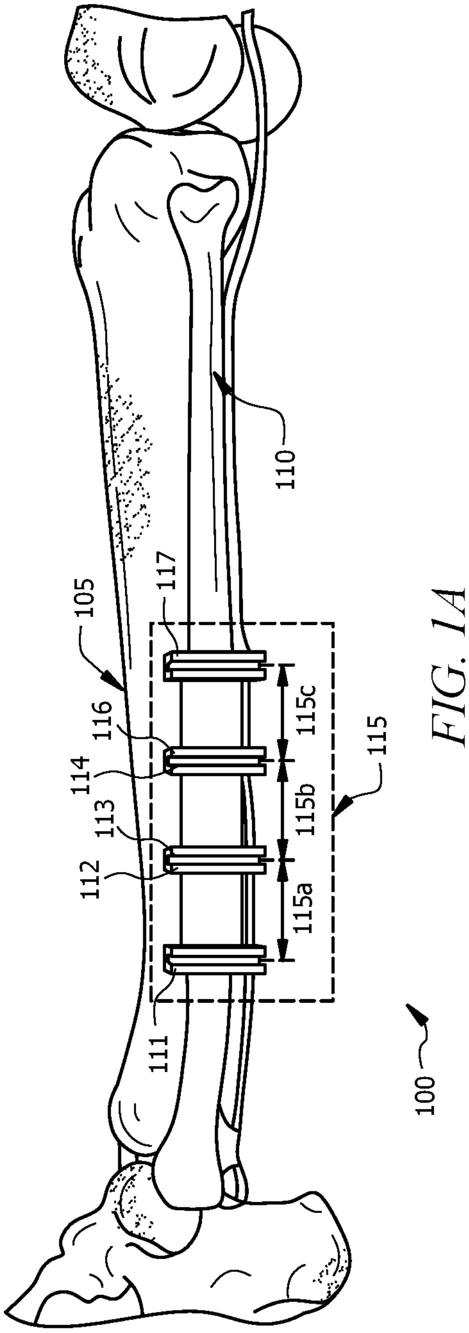
FIG. 1(*a*) depicts an anterior view of a patient's leg.
Figure 1B:
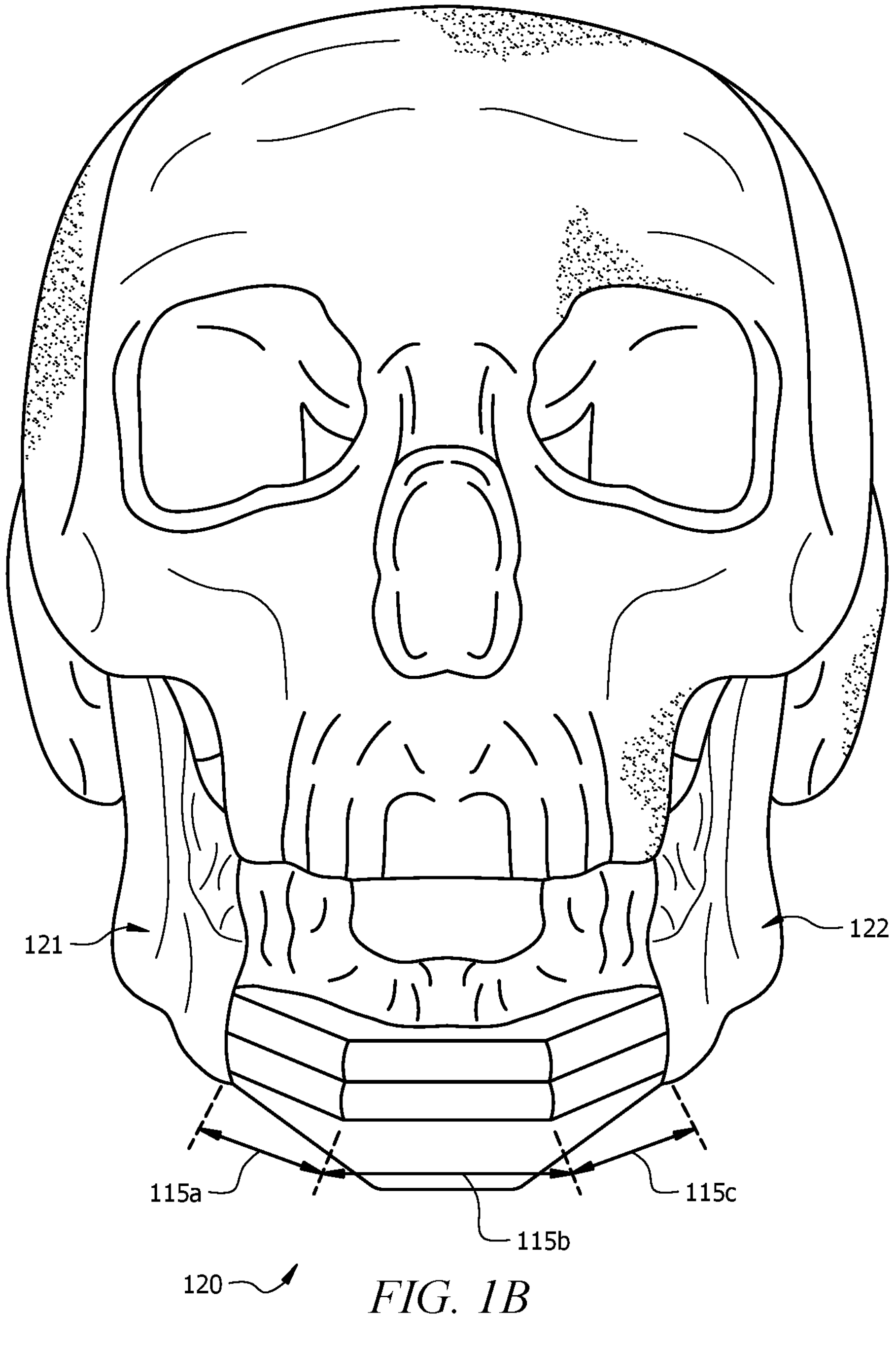
Figure 2A:
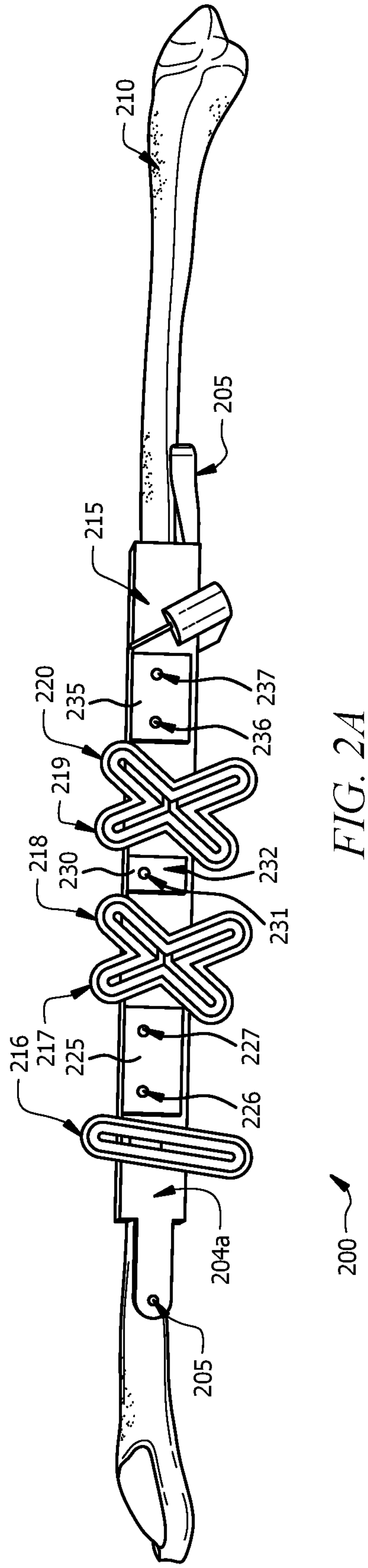
FIGS. 2(*a*)-2(*c*) depict a cutting guide (and portions thereof), in accordance with embodiments of the present disclosure.
Figure 2B:
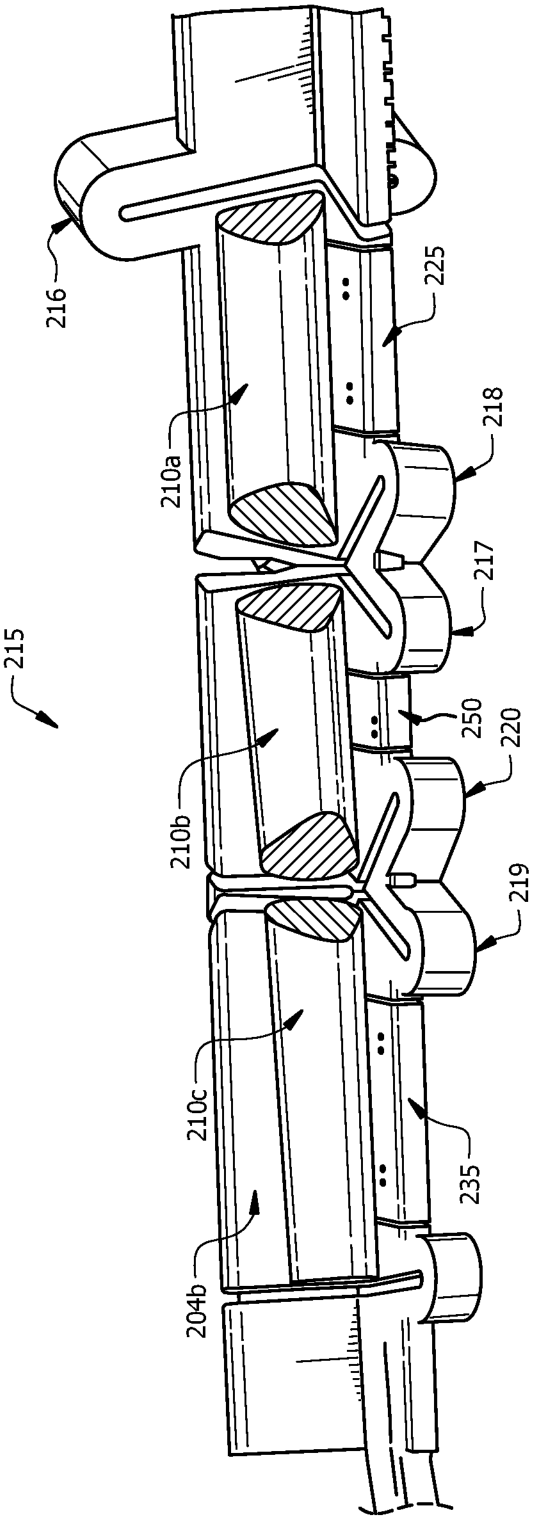
Figure 2C:
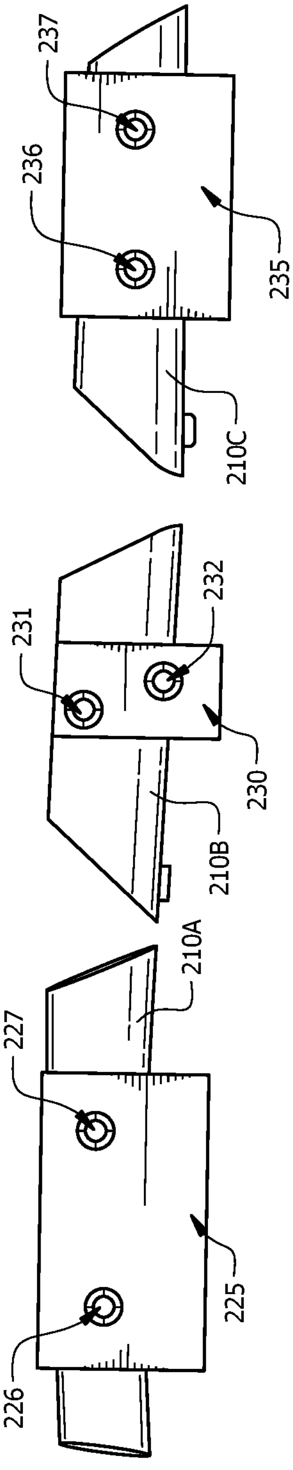

The disclosure first refers to FIGS. 2(*a*)-2(*c*), which depict a cutting guide (or a portion thereof) that may be used to resect one or more bones from a donor site. The disclosure then refers to FIGS. 3(*a*)-3(*c*), which depict a template guide that may be used by surgeon to facilitate reconstruction of the defect at the reconstruction site.

Referring now to FIG. 2(*a*), a 3D rendered image 200 of fibula 210 with cutting guide 215 positioned thereon is shown. Fibula 210 may be chosen by a surgeon during the planning phase of the reconstruction procedure, e.g., after determining that the cross-section of fibula 210 is substantially similar to the cross-section of the patient's original mandible bone. In other embodiments, the surgeon may choose a different bone from the patient's body, such as clavicle bone, hip bone, or ribs to reconstruct the mandibular defect. Cutting guide 215 may be designed to be positioned on fibula 210. For example, cutting guide 215 may include a contact surface designed to imitate or follow at least a portion of a contour of the donor bone (e.g., fibula 210). In aspects, at least a portion of the contour of the contact surface may be viewed as "a negative" of the surface of the underlying fibula 210. The imitating structure/design of the cutting guide 215 may help ensure proper positioning and orientation (e.g., during initial placement) of the cutting guide 215.

Cutting guide 215 defines apertures 205, which are designed to receive surgical fastening devices (e.g., surgical screws and/or wires) to secure cutting guide 215 to underlying fibula 210. In some embodiments, apertures 205 may be present on frontal and distal ends of fibula 210. In operation, a surgeon may use apertures 205 to secure cutting guide 215 at its proper position on the underlying bone. Cutting guide 215 may have top surface 204(*a*), which defines a plurality of cutting slots thereon, such as cutting slots 216-220. The cutting slots may be designed and dimensioned to receive a cutting blade of a cutting instrument (e.g., saw blade). In some embodiments, the design and orientation and/or shape and/or obliquity of the cutting slots 216-220 may depend on a desired bone-to-bone contact angle between the resected bones at the reconstruction site. For example, one or more of cutting slots 216-220 include slots that are oriented at specific angles so as to resect the underlying fibula 210 at angles that facilitate assembling the resected bones at the reconstruction site by having the desired bone-to-bone contact between the resected bones.

Cutting guide 215 may also include removable inserts 225, 230, and 235, which are designed to be able to be taken off or removed from the position occupied. In embodiments, the removable inserts forms a fit (e.g., snap-fit) with portions of guide 215 contiguous to the removable inserts. For example, for example, by exerting some force (e.g., by hands or using surgical hammer), the surgeon may remove removable inserts 225, 230, and 235 from their occupied positions. Removable inserts 225, 230, and 235, in embodiments, form interference-based connections (or fits) with portions of guide 215 contiguous to the removable inserts. An interference-based connection/fit, also sometimes referred to as a friction fit, is an example removable securing technique that connects two parts (e.g., removable inserts and the contiguous portions of the cutting guide 215), via friction, after the parts are pushed together, rather than by any other means of fastening. However, in other embodiments, a combination of interference fit and other means of fastening (e.g., surgical wires or screws, snap fit, and the like) may be used. The strength of interference required to connect or disconnect the two parts may result in different types of interference connections, such as a loose connection, or light interference connection. In some embodiments, the strength depends on the type of material used to manufacture the guide, the size of the connecting parts, and the desired degree of tightness. In other embodiments, the removable inserts may form connections with portions of guide 215 through other kinds of fits, such as a clearance fit. Examples of clearance fits include loose running fit, easy running fit, close running fit, etc. Achieving a clearance fit may require less force than a friction fit.

Removable inserts 225, 230, and 235 may define apertures thereon designed to receive surgical fastening devices (e.g., surgical screws and/or wires) to secure respective removable inserts to the underlying fibula 210. For example, removable insert 225 may include apertures 226 and 227; removable insert 230 may include apertures 231 and 232; and removable insert 235 may include apertures 236 and 237. In operation, after securing cutting guide 215 onto fibula 210, the surgeon may secure-using surgical fastening devices-removable inserts 225, 230, and 235 to fibula 210. The surgeon may then resect fibula 210 by using cutting tools via cutting slots 216-220 and form resected bones 210*a*, 210*b*, and 210*c*. The resected bones are depicted in FIG. 2(*b*), which shows a back view of cutting guide 215. The resected bones are secured to a second surface (or the contact surface) 204(*b*), which is the surface behind first surface 204(*a*), via surgical fastening devices that were used to secure removable inserts to fibula 210. Since resected bones 210*a*, 210*b*, and 210*c* are secured to removable inserts 225, 230, and 235, respectively, some force exerted to removable inserts 225, 230, and 235 may also remove the resected bones secured therewith (see FIG. 2(*c*)). In some embodiments, removable inserts may also include mating or connecting features, the use of which is described ahead.

Figure 3A:
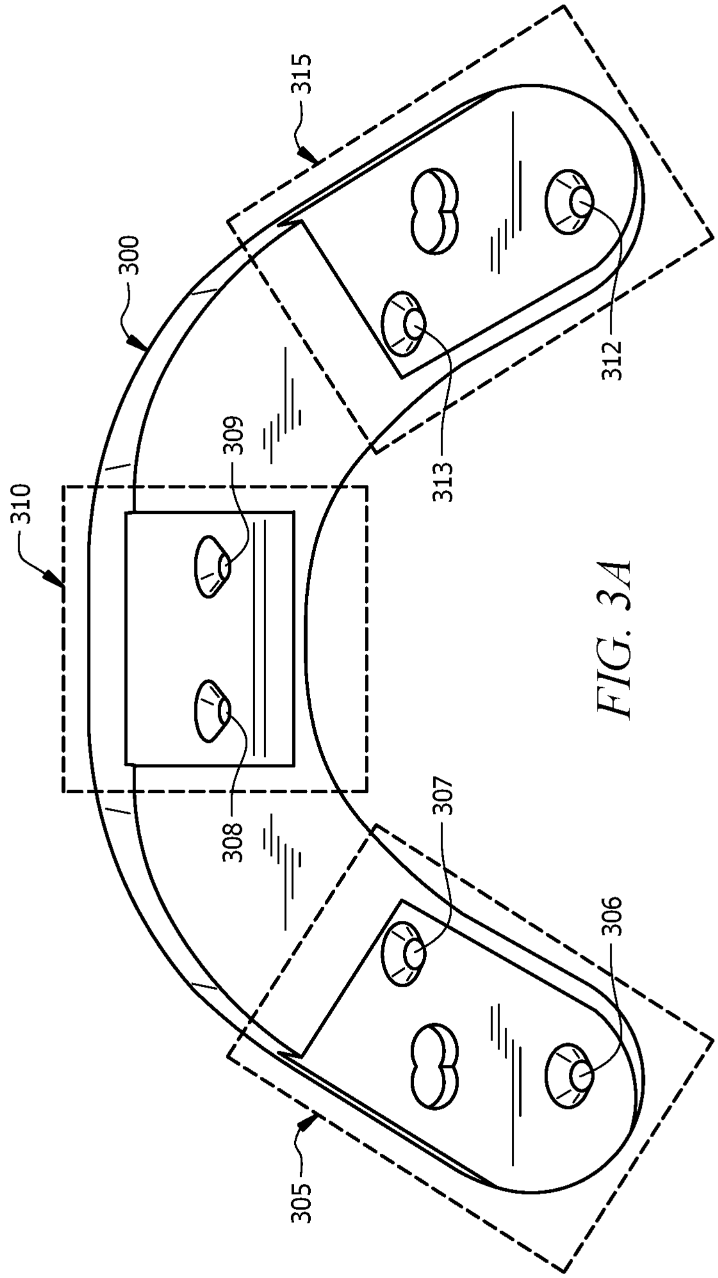
FIGS. 3(*a*)-3(*c*) depict a template guide that may be used by surgeon to facilitate reconstruction of a defect at the reconstruction site, in accordance with embodiments of the present disclosure.
Figure 3B:
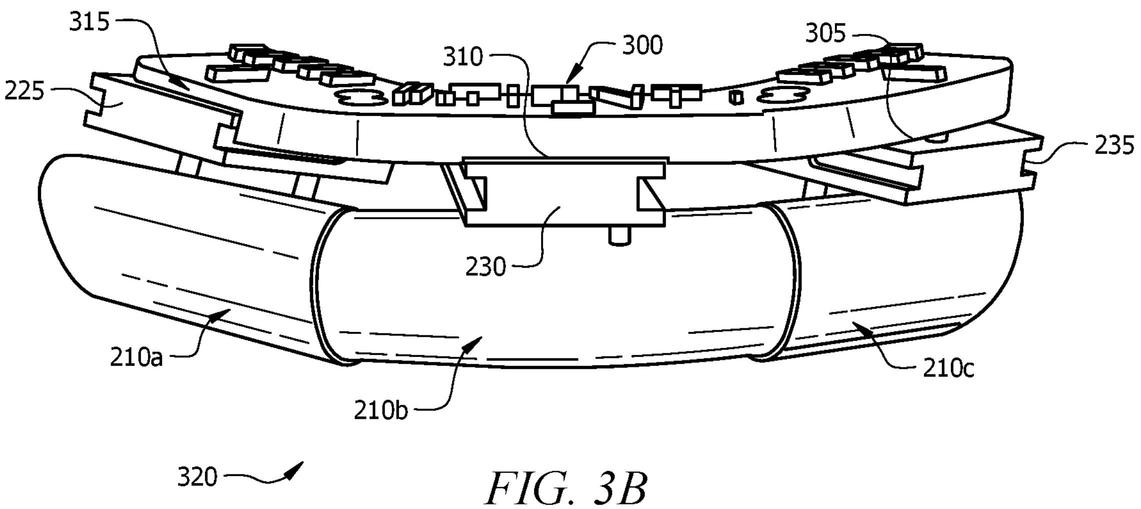
Figure 3C:
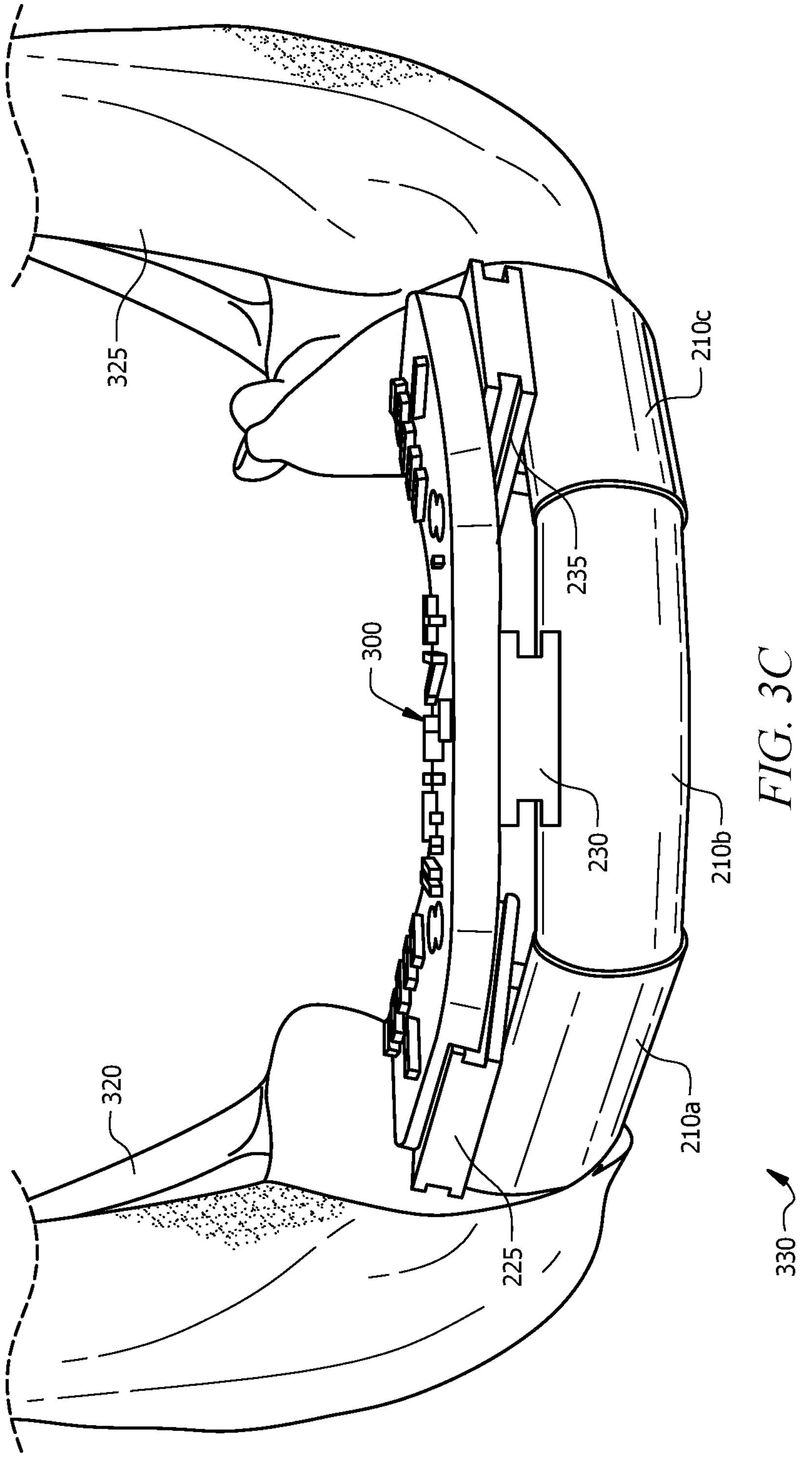

Referring to FIG. 3(*a*), template guide 300 that serves as a pattern that facilitates reconstructing the desired mandible defect is shown. Template guide 300 includes recess portions 305, 310, and 315, which are designed to mate (or couple) with the removable inserts so as to position or assemble the resected bones secured to the removable inserts at the reconstruction site. For instance, as shown in FIG. 3(*b*), removable insert 235 may couple with recess portion 305; removable insert 230 may couple with recess portion 310; and removable insert 225 may couple with recess portion 315. In some embodiments, the recessed portions include additional features that may strengthen the connection between removable inserts and the recessed portions. For example, recessed portion 310 include features 308 and 309, which are protruding features and are sized to fit with apertures 231 and 231, respectively, to improve the connection between recessed portion 310 and removable insert 230.

Template guide 300 is designed such that coupling the removable inserts with their respective recess portions assembles the resected bones at desired positions and reconstructs the curvature of the defective mandible. In embodiments, the recess portions are designed to mate with their respective removable inserts so as to connect the resected bones to their target angles (e.g., see FIG. 3(*b*)). For example, following resecting the fibula using the one or more of cutting slots 216-220 (which are oriented at specific angles so as to resect the underlying fibula 210 at angles that facilitate the desired bone-to-bone contact between the resected bones), the recessed portions mate with their respective removable inserts affixed with resected bones to connect the resected bone at their target angles.

In some embodiments, the coupling (or mating) of the removable inserts and their respective recessed portions may also form an interference-based connection. For example, to connect removable insert 230 with recess portion 310, the surgeon may slide (e.g., via tongue and groove type features) the mating feature of the removable insert 230 into the mating feature of the recess portion 310; and in order to disconnect removable insert 230 from the recessed portion 310, the surgeon may slide removable insert 230 out of recess portion 310. In other embodiments, removable inserts and recess portions may form other forms of fits, such as interference fit, clearance fit, button fit, snap fit, and the like.

Referring now to FIG. 3(*c*), with the improved surgical guide, the reconstruction may be performed by approximating the position of the complete structure shown in FIG. 3(*b*) to the left and right zygomatic bones 320 and 325, respectively and then affixing resected bones 210*a*, 210*b*, and 210*c* using surgical fastening devices, e.g., surgical screws and plates (not shown in FIG. 3(*c*)), to the zygomatic bones. The surgeon may first transplant the combined structure to the reconstruction site (i.e., the mandible region) where the surgeon may first fasten resected bones 210*a* to left zygomatic bone 320 and 210*c* to right zygomatic bone 210*c*. The surgeon may then complete the securing by fastening resected bone 210*b* with resected bones 210*a* and 210*c* using surgical plates and surgical fastening devices. After securing the resected bones, the surgeon may begin disassembling the combined structure. The disassembling process may include first removing template guide 300, e.g., by sliding it off the removable inserts, and then unscrewing the removable inserts from the resected bones, which may be followed by removing removable inserts.

Embodiments of surgical guide described above may be patient-specific. Patient-specific guides including a cutting guide and a template guide are individually designed and adapted to the patient's body anatomy such that, during reconstruction procedure, the surgeon would ultimately lead to a seamless donor bone and reconstruction bone continuity. However, in some cases, embodiments described above may provide for surgical guides which are not patient specific, meaning that the surgical guides are not designed for a specific patient, but are generically designed. Thus, the same design can be used to produce multiple surgical guides, which can further be used during reconstruction procedures of different patients. In some embodiments, these non-patient-specific surgical guides may be designed based on age, gender, or generic physical makeup of the human anatomical structure. As such, the non-patient-specific surgical guides may come in different sizes, e.g., small-male, small-female, medium-male, medium-female, large-male, and large-female. By way of example, a medium-male design may be used during a reconstruction procedure of a 5 foot 6 inch, 30 year old man, whereas, a large-male design may be used during a reconstruction procedure of a 6 foot, 30 year old man.

Figure 4:
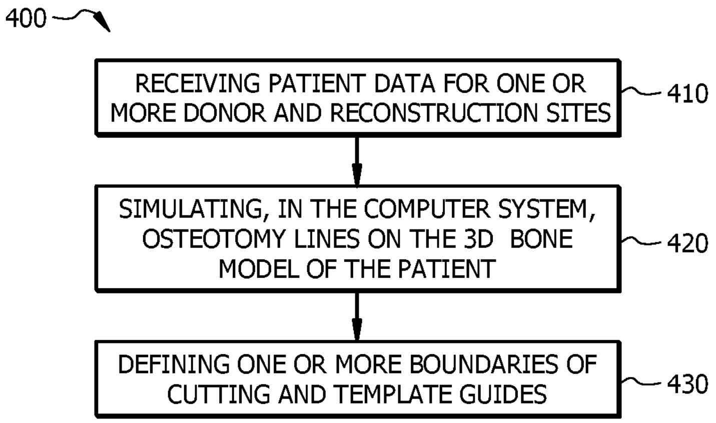
FIG. 4 depicts an illustrative method that may be used to design and manufacture patient-specific surgical guides, in accordance with embodiments of the present disclosure.

FIG. 4 depicts an illustrative method 400 that may be used to design and manufacture patient-specific surgical guides. In some cases, method 400 may be performed, without limitation, by a medical institution (e.g., a hospital) where the reconstruction surgery will eventually take place. In other cases, method 400 may be performed by a contracted third party (e.g., a medical device company) that works with the medical institution to generate and manufacture patient-specific surgical guides.

In some embodiments, method 400 begins with block 410 that includes receiving a patient's data for one or more donor and reconstruction sites. Patient-specific information, in some examples, includes one or more electronic images and/or measurements of the surface of both the donor site (e.g., fibula) and the reconstruction site (e.g., mandible region). Images and measurements of both sites, in one embodiment, may provide coordinates that define the surface and shape of the sites. The electronic images of the sites may be from, without limitation, a CT image, a spiral CT image, an MRI image, an ultrasound scan, digital tomosynthesis, or optical coherence tomography. The received patient data, in one embodiment, may then be utilized to generate 3D bone models of both the donor and reconstruction sites. The 3D bone model, in one embodiment, is generated using a computer system configured to receive the images and/or other details and generate the bone model (e.g., of both the fibula and the mandible) using a software system installed in the computer system. The 3D bone model may then be subsequently used in surgical planning by the surgeon performing the procedure. The surgical planning may include discussions regarding the amount of bone resection required (from the clinical and radiological data, i.e., CT scan and MRI) considering at least some (e.g., 3 cm) margin for the osteotomy to fix the plates to the resected bones; the side of fibula that will be used to resect the bones (e.g., the top side, bottom side, etc.); the number of resected bones and bone lengths; fibula and customized plate in setting and final position in relation to the remaining mandible and craniofacial skeleton; the degree of obliquity of the osteotomies both on the mandible and fibula; the number and position of screw holes both on the mandible and fibular segments; and the shape and position of cutting guides.

Method 400 may then move to block 420 that includes simulating, in the computer system, osteotomy lines on the 3D bone model of the patient. In some cases, the surgeon may virtually operate (e.g., resect) on the donor bone and reconstruct, at the reconstruction site, the desired bone structure using the resected bones. Method 400 may then move to block 430 that includes generating cutting and template guides that will be used by the surgeon during the procedure. In some embodiments, block 430 includes defining one or more boundaries of both the cutting and template guides. The boundaries of the guides, in some embodiments, are based on one or more input parameters, which may be provided by the surgeon. In some embodiments, the user of block 410 extrapolates relevant input parameters from the images and/or other details received in block 410. In some embodiments, the parameters may include minimum and maximum thicknesses of the desired bone, size of the osteotomy line, and the size of the apertures.

In one embodiment, surgical guides are manufactured using additive technology or freeform fabrication. In this method of manufacture, the surgical guides are formed through successive fusion of chosen parts of powder layers applied to a worktable. In some embodiments, PA 12 (also known as Nylon 12) is used as the powder. The surgical guides formed using PA 12 have high tensile strength, impact strength, and are able to flex without fracture. In other embodiments, other types of material may be used. In summary, once the patient-specific information is ascertained, rapid prototyping or other manufacturing techniques may be used to adapt the surgical guide to the patient's particular biological structure. In some embodiments, a mold may be made to form the surgical guide. In some embodiments, a surgical guide may be manufactured using a 3D printing technology disclosed in co-pending U.S. patent application Ser. No. 16/378,446, entitled "System and Method for Forming Material Layers for Surgical Applications," and filed by the assignee of the present application on Apr. 8, 2019. The disclosure of U.S. patent application Ser. No. 16/378,446 is incorporated by reference herein in its entirety.

The surgical guides manufactured using the techniques described above may be disposed in a packaging unit. The packaging unit may include a contoured unit having a contoured surface that matches a contour of the biological structure (e.g., bone, such as mandible bone) on which a surgeon would operate. For example, the contoured unit may have contour surfaces of both the donor site (e.g., fibula) and the reconstruction site (e.g., the mandible). The contoured unit may be 3D print of metal, plastic, poly-ether-ether-ketone (PEEK) material, etc. in the same or similar manner as described in U.S. patent application Ser. No. 16/378,446. As such, the surgical guides may be disposed onto the contoured unit and provide a visual aid to the surgeon before the surgery. In some embodiments, the contoured unit also has one or more features that would further facilitate the surgery by providing a visual aid to the surgeon. For example, the contoured unit may have one or more features, such as apertures, which may be holes for receiving surgical screws that are selected based on thickness/depth of bone exhibiting the contour in the 3D model of the desired bone of a patient. Additionally, the contoured unit may be a part of a surgical kit that includes other medical devices (e.g., bone plates) that may be used during the surgery. In some embodiments, the packing unit includes a lid that may have a reverse contour, which is designed to mate with the contour of the surface of the contoured unit in such a way that the contoured unit and the guide(s) and/or other medical devices (e.g., bone plates and surgical screws) are secured in place when the lid is connected to the contoured unit.

As an example, the surgical unit may include a first guide (e.g., cutting guide) having a contact surface (e.g., second surface 204(*b*)). In embodiments, the contact surface of the first guide may match a first contoured surface of the surgical kit, which further matches a contour of the biological structure (e.g., fibula) on which a surgeon would operate to carve out the resected bones. The surgical kit may also include a second guide (e.g., template guide) having a contact surface that matches a second contoured surface of the surgical kit, which further matches a contour of the biological structure (e.g., mandible bone or a portion thereof) on which a surgeon would operate.

Figure 5:
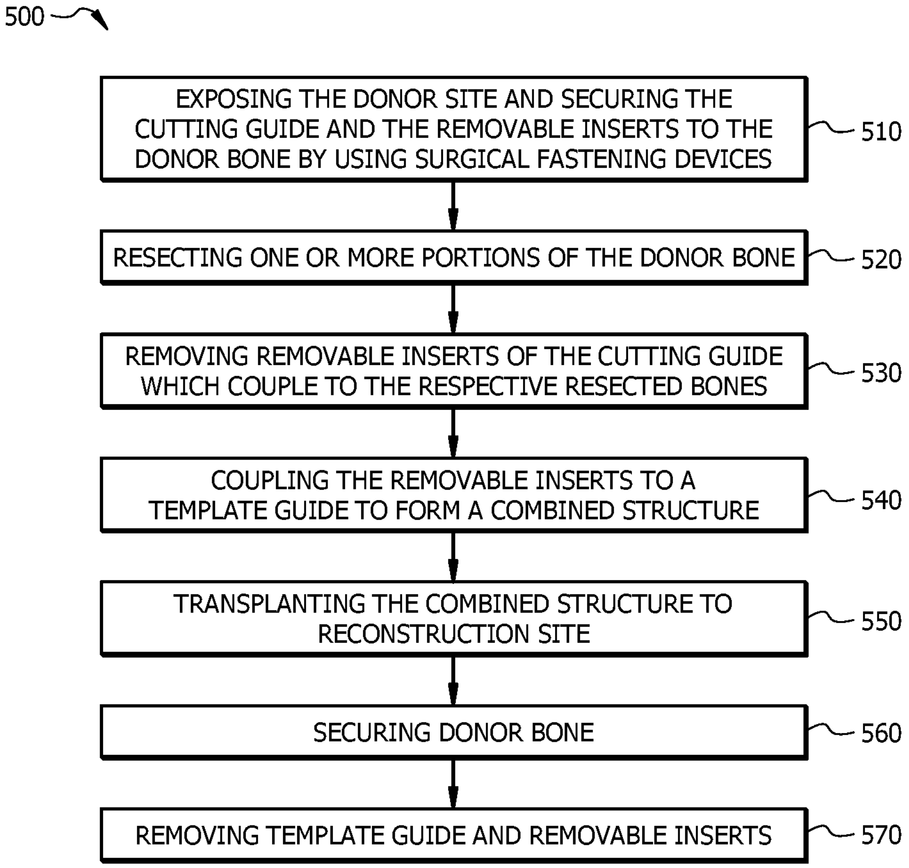
FIG. 5 depicts an illustrative method that may be implemented by a surgeon using the surgical guides during a reconstruction procedure, in accordance with embodiments of the present disclosure.

Refer now to FIG. 5, which depicts an illustrative method 500 that may be implemented by a surgeon using the surgical guides during a reconstruction procedure. In one embodiment, method 500 begins with block 510 that includes exposing the donor site and securing the cutting guide and the removable inserts to the donor bone by using surgical fastening devices. The method 500 may then move to block 520 that includes resecting one or more portions of the donor bone (e.g., fibula bone is resected using the cutting guide to extract resected fibula bone portions). Once the donor bone is resected, the surgeon may move to block 530 that includes removing removable inserts of the cutting bone, where the removable inserts couple to the respective resected bones. The surgeon may then move to block 540 that includes coupling the removable inserts to a template guide to form a combined structure (such as shown in FIG. 3(*b*)) including the template guide, the removable inserts, and the resected bones. The combined structure is then transplanted to the reconstruction site (block 550) where the surgeon may fasten (block 560) the resected bones to the left and right zygomatic bones using surgical plates and surgical fastening devices. After securing the resected bones, the surgeon may move to block 570, which may include removing the template guide by sliding it off the removable inserts. Block 570 may then include unscrewing the removable inserts from the resected bones and then removing removable inserts, thereby reconstructing the mandible.

As noted above, the guides may be patient-specific, and the patient's data may be received by a computer system and stored in a computer-readable medium in the computer system. A method of manufacturing the surgical guide using the patient's data stored in computer-readable medium is now described. The method of manufacturing may include accessing a computer-readable medium having stored thereon one or more three-dimensional (3D) images of a guide and fabricating the guide based on the one or more 3D images. In embodiments, the fabricating the surgical guide may include fabricating the cutting guide 215 having cutting slots (e.g., cutting slots 216-220), removable inserts (e.g., insert 225), and apertures (e.g., 205). In embodiments, the fabricating the guide may further include fabricating the template guide 300 having features designed to mate with the removable inserts of the cutting guide. In embodiments, removable inserts designed to disconnect from the cutting guide upon application of force at a first instance and couple with the template guide upon application of a force at a second instance.

Although embodiments of the present application and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. Moreover, the scope of the present application is not intended to be limited to the particular embodiments of the process, machine, manufacture, composition of matter, means, methods and steps described in the specification.

The invention claimed is:

1. A pre-packaged surgical guide kit, comprising:

a cutting guide configured to be placed over a fibula and facilitate extraction of one or more resected fibula bone portions, the cutting guide including one or more removable inserts configured to be removably coupled in a direct manner to the cutting guide, each of the removable inserts comprises an aperture, wherein each of the one or more resected fibula bone portions is configured to be secured with a removable insert of the one or more removable inserts;

a template guide configured to be positioned at a mandibular reconstruction site and configured to mate with the one or more removable inserts and to align the one or more resected fibula bone portions to reconstruct at least part of a mandible, the template guide comprising a top surface and a bottom surface defining a plurality of features, each of the removable inserts is configured to mate with one of the features so as to connect a plurality of resected bones to their target angles, wherein a majority of each of the removable inserts is covered by the bottom surface of the template guide when each of the removable inserts is mated with one of the features; and a packaging unit comprising a first contoured surface and a second contoured surface, wherein the first contoured surface matches a contour of the fibula and the second contoured surface matches a contour of the mandible, and wherein the cutting guide includes a first contact surface matching the first contoured surface and the template guide includes a second contact surface matching the second contoured surface.

2. The kit of claim 1, wherein the fibula comprises a donor site.

3. The kit of claim 1, wherein the first contoured surface and/or the second contoured surface are patient-specific anatomic contours.

4. The kit of claim 3, wherein the first contact surface and/or the second contact surface are patient-specific anatomic contours.

5. The kit of claim 3, wherein the packaging unit is 3D printed based on patient-specific imaging data.

6. The kit of claim 1, wherein the first guide and the second guide are disposed onto the first contoured surface and the second contoured surface of the packaging unit, respectively, to provide a visual aid to a surgeon.

7. The kit of claim 1, further comprising surgical screws, wherein the packaging unit further comprise apertures configured to receive the surgical screws.

8. The kit of claim 7, wherein the surgical screws are selected based on a thickness or depth of a patient's first or second biological structures.

9. The kit of claim 1, wherein the packaging unit further comprises a lid including a reverse contour.

10. The kit of claim 1, further comprising one or more bone plates.

* * * * *